United States Patent
Cui (10) Patent No.: US 11,945,164 B2
(45) Date of Patent: Apr. 2, 2024

(54) METHOD FOR MANUFACTURING MICRONEEDLE BIOSENSOR

(71) Applicant: Peking University, Beijing (CN)

(72) Inventor: Yue Cui, Beijing (CN)

(73) Assignee: PEKING UNIVERSITY

( * ) Notice: Subject to any disclaimer, the term of this patent is extended or adjusted under 35 U.S.C. 154(b) by 0 days.

(21) Appl. No.: 17/944,216

(22) Filed: Sep. 14, 2022

(65) Prior Publication Data

US 2023/0078221 A1    Mar. 16, 2023

(30) Foreign Application Priority Data

Sep. 14, 2021    (CN) .......................... 202111075848.7

(51) Int. Cl.
| | |
|---|---|
| B33Y 10/00 | (2015.01) |
| B29C 64/30 | (2017.01) |
| B33Y 40/20 | (2020.01) |
| B33Y 80/00 | (2015.01) |
| B41M 3/00 | (2006.01) |
| G01N 27/30 | (2006.01) |

(Continued)

(52) U.S. Cl.
CPC .............. *B29C 64/30* (2017.08); *B33Y 10/00* (2014.12); *B33Y 40/20* (2020.01); *B33Y 80/00* (2014.12); *B41M 3/006* (2013.01); *G01N 27/308* (2013.01); *G01N 27/3271* (2013.01); *B29L 2031/752* (2013.01)

(58) Field of Classification Search
None
See application file for complete search history.

(56) References Cited

U.S. PATENT DOCUMENTS

| | | | |
|---|---|---|---|
| 2002/0133129 A1* | 9/2002 | Arias ............... | A61B 5/150419 264/225 |
| 2013/0225956 A1* | 8/2013 | Huang ................ | A61B 5/0537 600/345 |

(Continued)

OTHER PUBLICATIONS

Sharma et al, Evaluation of a minimally invasive glucose biosensor for continuous tissue monitoring, Anal Bioanal Chem. Nov. 2016;408(29):8427-8435. doi: 10.1007/s00216-016-9961-6. Epub Oct. 15, 2016 (Year: 2016).*

*Primary Examiner* — Yung-Sheng M Tsui
(74) *Attorney, Agent, or Firm* — Jose Cherson Weissbrot (57) ABSTRACT

A microneedle biosensor includes a microneedle and a substrate. One end of the microneedle is connected to the substrate, an outer surface of the microneedle is provided with a working electrode and a first electrode, an outer surface of the working electrode is provided with an enzyme, and an outer surface of the microneedle biosensor is covered with a biocompatible film. A method for manufacturing a microneedle biosensor includes: manufacturing the substrate and the microneedle in an additive mode simultaneously; spray-printing and curing the working electrode and the first electrode on the outer surface of the microneedle; spray-printing and drying the enzyme on the outer surface of the working electrode; and using biocompatible liquid for spray-printing, and drying the biocompatible liquid to form the biocompatible film. The substrate, the microneedle, the working electrode, the first electrode, the enzyme and the biocompatible film are all manufactured through a full printing method.

13 Claims, 9 Drawing Sheets

(51) Int. Cl.
    *G01N 27/327*     (2006.01)
    *B29L 31/00*     (2006.01)

(56) References Cited

U.S. PATENT DOCUMENTS

| | | | |
|---|---|---|---|
| 2015/0208984 A1* | 7/2015 | Huang | H01L 21/02463 |
| | | | 600/393 |
| 2016/0166184 A1* | 6/2016 | Teng | A61B 5/150282 |
| | | | 600/347 |
| 2020/0029869 A1* | 1/2020 | Cho | A61B 5/14514 |
| 2022/0015668 A1* | 1/2022 | Pennathur | A61B 5/685 |
| 2022/0031244 A1* | 2/2022 | Windmiller | A61B 5/0022 |
| 2022/0257181 A1* | 8/2022 | Wang | A61B 5/14532 |
| 2022/0287598 A1* | 9/2022 | Pierart | A61M 37/0015 |
| 2022/0361776 A1* | 11/2022 | Wang | A61B 5/002 |
| 2023/0023786 A1* | 1/2023 | Crespo Paravano | |
| | | | A61B 5/14514 |

\* cited by examiner

METHOD FOR MANUFACTURING MICRONEEDLE BIOSENSOR

CROSS REFERENCE TO THE RELATED APPLICATIONS

This application is based upon and claims priority to Chinese Patent Application No. 202111075848.7, filed on Sep. 14, 2021, the entire contents of which are incorporated herein by reference.

TECHNICAL FIELD

The present disclosure relates to the technical field of medical instruments, in particular to a method for manufacturing a microneedle biosensor.

BACKGROUND

A commercial dynamic glucometer has a glucose sensor with a soft needle several millimeters long, and the soft needle is brought and inserted by a hard needle and then continuously measures the concentration of glucose in tissue fluid in vivo. Such a measurement mode faces the following problems and challenges: (1) Skin pain and trypanophobia exist. In order to bring the soft needle into the skin, the hard needle with several millimeters long needs to be inserted into the skin, and the use of the hard needle can cause the trypanophobia and can cause pain in the skin. (2) A wound is deep, large in area and long in healing time. After the needle is inserted into the skin, the wound is deep, large in area and long in healing time since the needle is long. (3) A risk of infection is high. After traditional hard needle insertion, there is a risk of infection due to local skin tissue damage, local swelling, secretion, or suppuration may also occur, and marks or scars may be left at the needle site. (4) Current dynamic glucometers are generally high in price. The price of a common glucometer sensor test paper for measuring fingertip blood is about 0.1 USD, and the price of a dynamic glucometer sensor is about a hundred US dollars.

Research on a novel non-painful/slightly-painful, safer and cheaper biosensor for dynamic monitoring of glucose or other body fluid analytes in tissue fluid will bring better experience to patients, so the sensor can be used more widely and can be more positive and effective on disease management, especially diabetes mellitus management.

A microneedle system can provide a semi-invasive disease treatment and measurement mode. Moreover, compared with the traditional long needle, the microneedle system reduces the pain of a patient, and reduces the wound depth and area and the risk of cross infection. However, in the prior art, the used sensor manufacturing process is complex in method, high in price and long in time consumption.

SUMMARY

Therefore, the present disclosure provides a method for manufacturing a microneedle biosensor, to solve or partially solve the problems of complicated process method, high price and long-time consumption of biosensor manufacturing in the prior art.

In order to achieve the above objective, the technical solution of the present disclosure is achieved as follows:

According to a method for manufacturing a microneedle biosensor, the microneedle biosensor includes a microneedle and a substrate, where one end of the microneedle is connected to the substrate, an outer surface of the microneedle is fabricated with a working electrode and a first electrode, an outer surface of the working electrode is immobilized with enzyme, and an outer surface of the microneedle biosensor is covered with a biocompatible film; and the method for manufacturing a microneedle biosensor includes:
  manufacturing the substrate and the microneedle in an additive mode simultaneously;
  spray-printing and curing the working electrode and the first electrode on the outer surface of the microneedle;
  spray-printing and drying the enzyme on the outer surface of the working electrode; and
  using biocompatible liquid for spray-printing, and drying the biocompatible liquid to form the biocompatible film.

Optionally, the first electrode includes a counter electrode and a reference electrode, and the spray-printing the working electrode and the first electrode on the outer surface of the microneedle further includes:
  spray-printing and curing the working electrode and the counter electrode on the outer surface of the microneedle simultaneously, and
  spray-printing and curing the reference electrode on the outer surface of the microneedle; and alternatively,
  spray-printing and curing the reference electrode on the outer surface of the microneedle, and
  spray-printing and curing the working electrode and the counter electrode on the outer surface of the microneedle simultaneously.

Optionally, at least three microneedles are provided, and the working electrode, the counter electrode and the reference electrode correspond one-to-one to the microneedles.

Optionally, one microneedle is provided and has a pyramidal structure, and the working electrode, the counter electrode and the reference electrode correspond one-to-one to surfaces of the microneedle.

Optionally, the working electrode is spray-printed by using a first ink, the counter electrode is spray-printed by using a second ink, and the first ink and the second ink are both made of a nanogold composite material, or a nanoplatinum composite material, or a nanocarbon composite material.

Optionally, the reference electrode is spray-printed by using a third ink, and the third ink is a nanoscale silver/silver chloride composite ink.

Optionally, the spray-printing the working electrode and the first electrode on the outer surface of the microneedle includes:
  spray-printing and curing the working electrode on the outer surface of the microneedle, and
  spray-printing and curing the first electrode on the outer surface of the microneedle, where the first electrode is used as both a reference electrode and a counter electrode; and alternatively,
  spray-printing and curing the first electrode on the outer surface of the microneedle, and
  spray-printing and curing the working electrode on the outer surface of the microneedle.

Optionally, at least two microneedles are provided, and the working electrode and the first electrode correspond one-to-one to the microneedles.

Optionally, one microneedle is provided and has a pyramidal structure, and the working electrode and the first electrode correspond one-to-one to surfaces of the microneedle.

Optionally, the working electrode is spray-printed by using a first ink, and the first electrode is spray-printed by using a third ink.

Optionally, the first ink contains an electron mediator.

Optionally, the spray-printing enzyme on the outer surface of the working electrode uses a printing enzyme complex solution.

According to the method for manufacturing a microneedle biosensor, the substrate and the microneedle are manufactured in an additive mode simultaneously, the working electrode and the first electrode are spray-printed on the outer surface of the microneedle, and the enzyme is spray-printed on the outer surface of the working electrode; and the substrate, the microneedle, the working electrode, the first electrode, the enzyme and the biocompatible film are all manufactured through a full printing method, such that the manufacturing method is simple, the price is low, and time consumption is short.

The above description is merely an overview of the technical solutions of the present disclosure. In order to more clearly understand the technical means of the present disclosure, the present disclosure can be implemented according to the contents of the specification, and in order to make the above and other objects, features and advantages of the present disclosure more obvious and comprehensible, specific implementation modes of the present disclosure are particularly given below.

BRIEF DESCRIPTION OF THE DRAWINGS

In order to more clearly illustrate technical solutions in the specific implementation modes of the present disclosure or in the prior art, a brief introduction to the accompanying drawings required for the description of the specific implementation modes or the prior art will be provided below. Obviously, the accompanying drawings in the following description are some of the implementation modes of the present disclosure, and those ordinary skill in the art would also be able to derive other accompanying drawings from these accompanying drawings without making creative efforts.

BRIEF DESCRIPTION OF THE REFERENCE NUMBERS

1—substrate; 2—working electrode; 3—counter electrode; 4—reference electrode; 5—first electrode; and 6—microneedle.

DETAILED DESCRIPTION OF THE EMBODIMENTS

The technical solutions of the present disclosure will be described below clearly and comprehensively in conjunction with the drawings. Apparently, the embodiments described are merely some of, rather than all of, the embodiments of the present disclosure. Based on the embodiments of the present disclosure, all other embodiments acquired by those of ordinary skill in the art without making creative efforts fall within the scope of protection of the present disclosure.

In the description of the present disclosure, it is to be noted that the terms "central", "upper", "lower", "left", "right", "vertical", "horizontal", "inner", "outer", etc. indicate azimuthal or positional relations based on those shown in the drawings only for ease of description of the present disclosure and for simplicity of description, and are not intended to indicate or imply that the referenced device or element must have a particular orientation and be constructed and operative in a particular orientation, and thus may not be construed as a limitation on the present disclosure. Moreover, the terms "first", "second", "third", etc. are merely for descriptions and may not be understood as indication or implication of relative importance.

Figure 1:
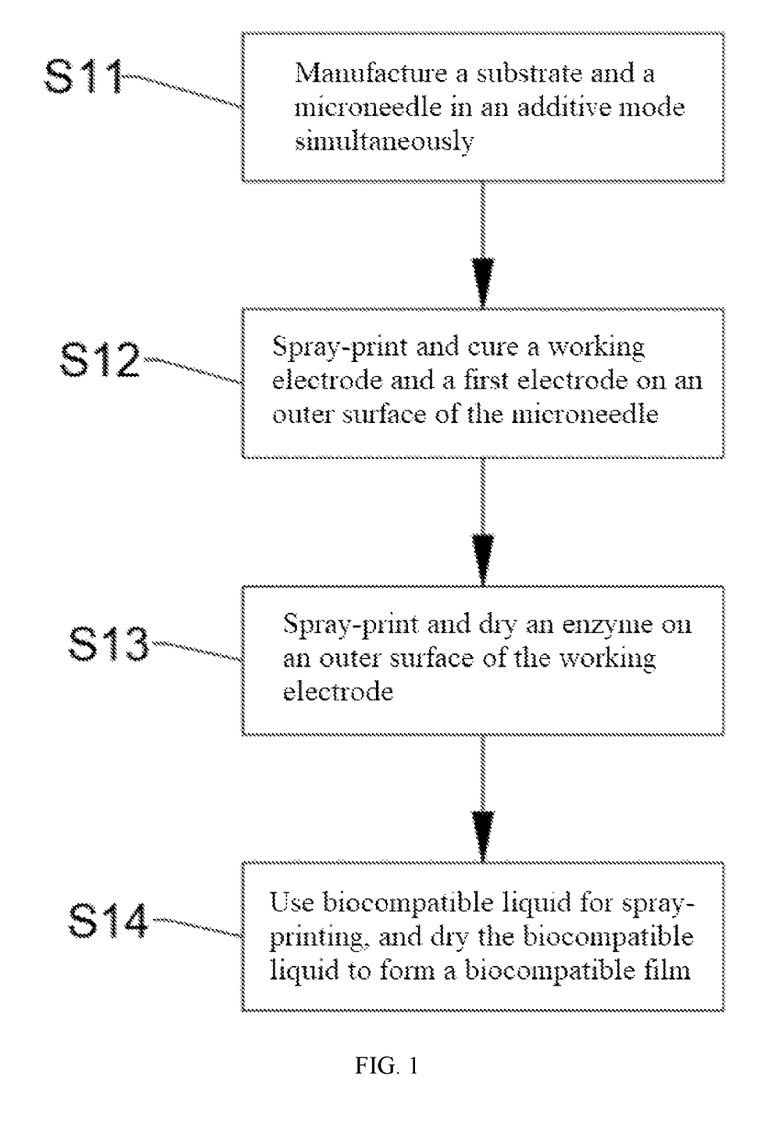
FIG. 1 is a flowchart of the first method for manufacturing a microneedle biosensor according to the present disclosure.

As shown in FIG. 1, disclosed in an embodiment of the present application is a method for manufacturing a microneedle biosensor. The microneedle biosensor includes a microneedle 6 and a substrate 1, where one end of the microneedle 6 is connected to the substrate 1, an outer surface of the microneedle 6 is fabricated with a working electrode 2 and a first electrode 5, an outer surface of the working electrode 2 is immobilized with an enzyme, and an outer surface of the microneedle biosensor is covered with a biocompatible film. The method for manufacturing a microneedle biosensor includes:

S11, manufacture the substrate 1 and the microneedle 6 in an additive mode simultaneously;

S12, spray-print and cure the working electrode 2 and the first electrode 5 on the outer surface of the microneedle 6;

S13, spray-print and dry the enzyme on the outer surface of the working electrode 2; and S14, use biocompatible liquid for spray-printing, and dry the biocompatible liquid to form the biocompatible film.

Specifically, additive manufacturing (AM) is commonly known as 3D printing, which is a manufacturing technology that fuses computer aided design and material machining and forming technologies, is based on a digital model file, and stacks a special metal material, a non-metal material and a medical biological material layer by layer by means of software and a numerical control system according to the modes of extrusion, sintering, melting, photocuring, jetting, etc., so as to manufacture a physical object. Machining procedures may be greatly reduced, and a machining period may be shortened.

Spray-printing refers to a printing mode in which a liquid ink is sprayed from a spray head to a support by power, for example, gas. In this embodiment of the present application, spray-printing refers to that the liquid ink is sprayed from the spray head to the microneedle 6, and the liquid ink forms the working electrode 2 and the first electrode 5 on the microneedle 6.

The biosensor has a small size. During spray-printing, the spray head needs to be a set distance away from the microneedle 6. For example, the spray head conducts spray-printing on a side surface of the microneedle 6, so as to guarantee a spray-printing effect. Spray-printing is carried out according to actual printing requirements.

According to the method for manufacturing a microneedle biosensor in the embodiment of the present application, the substrate 1 and the microneedle 6 are manufactured in an additive mode simultaneously, the working electrode 2 and the first electrode 5 are spray-printed on the outer surface of the microneedle 6, and the enzyme is spray-printed on the outer surface of the working electrode 2; and the substrate 1, the microneedle 6, the working electrode 2, the first electrode 5, the enzyme and the biocompatible film are all manufactured through a full printing method, such that the manufacturing method is simple, the price is low, and the time consumption is short.

Figure 2:
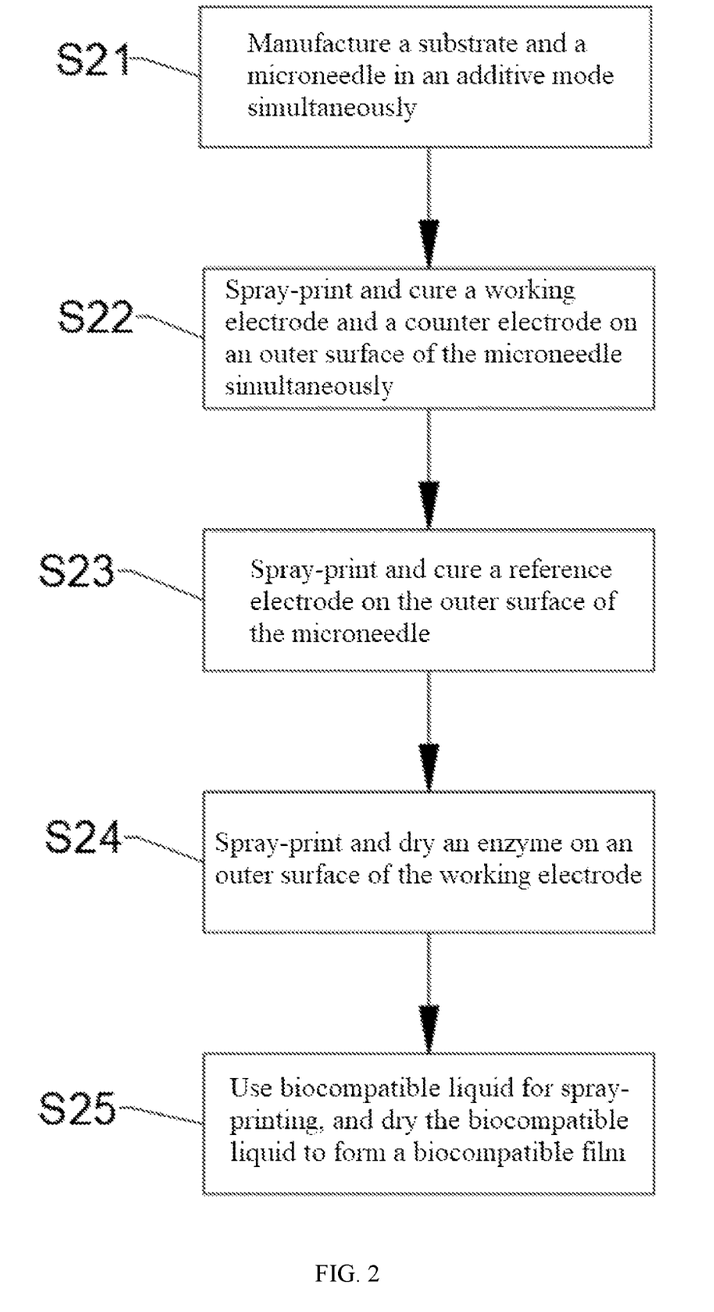
FIG. 2 is a flowchart of the second method for manufacturing a microneedle biosensor according to the present disclosure.

As shown in FIG. 2, in an embodiment, the first electrode 5 includes a counter electrode 3 and a reference electrode 4. The method for manufacturing a microneedle biosensor includes:
  S21, manufacture a substrate 1 and a microneedle 6 in an additive mode simultaneously;
  S22, spray-print and cure a working electrode 2 and the counter electrode 3 on an outer surface of the microneedle 6 simultaneously;
  S23, spray-print and cure the reference electrode 4 on the outer surface of the microneedle 6;
  S24, spray-print and dry an enzyme on an outer surface of the working electrode 2; and
  S25, use biocompatible liquid for spray-printing, and dry the biocompatible liquid to form the biocompatible film.

When the first electrode 5 includes the counter electrode 3 and the reference electrode 4, the working electrode 2, the counter electrode 3 and the reference electrode 4 are components in an electrochemical system, that is, components in a three-electrode system, and may be used in disease measurement, for example, measurement of glucose concentration in tissue fluid so as to dynamically monitor diabetes mellitus.

In actual production, two printing apparatuses are selected for printing, the working electrode 2 and the counter electrode 3 are spray-printed on the first apparatus, and the reference electrode 4 is spray-printed on the second apparatus.

In S25, the outer surfaces of the substrate 1, the microneedles 6, the working electrode 2, the counter electrode 3, the reference electrode 4, and the enzyme are spray-printed by using biocompatible liquid and dried to form a biocompatible film.

Figure 3:
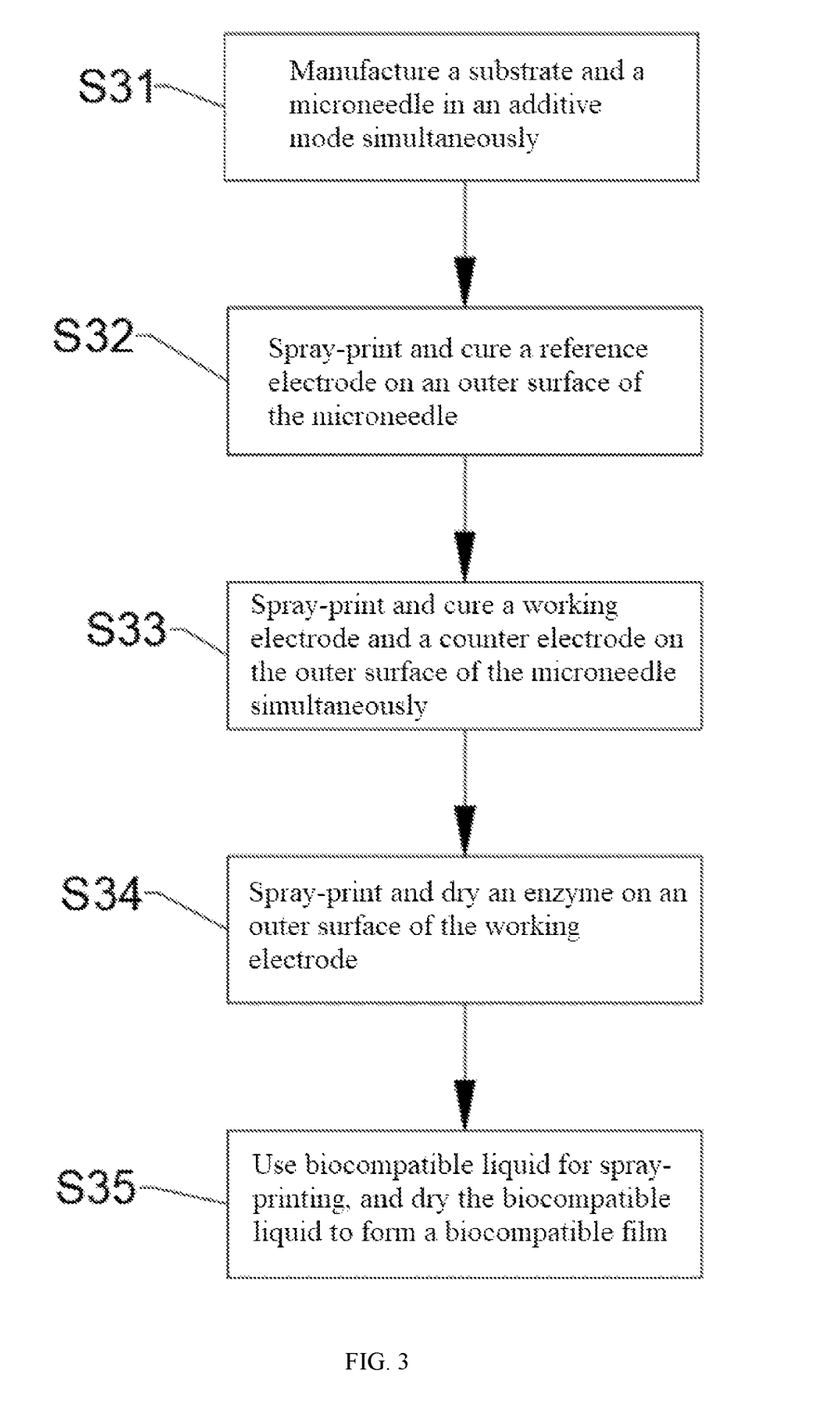
FIG. 3 is a flowchart of the third method for manufacturing a microneedle biosensor according to the present disclosure.

As shown in FIG. 3, in another embodiment, the first electrode 5 includes a counter electrode 3 and a reference electrode 4. The method for manufacturing a microneedle biosensor includes:
  S31, manufacture a substrate 1 and a microneedle 6 in an additive mode simultaneously;
  S32, spray-print and cure the reference electrode 4 on an outer surface of the microneedle 6;
  S33, spray-print and cure a working electrode 2 and the counter electrode 3 on the outer surface of the microneedle 6 simultaneously;
  S34, spray-print and dry an enzyme on an outer surface of the working electrode 2; and
  S35, use biocompatible liquid for spray-printing, and dry the biocompatible liquid to form the biocompatible film.

In actual production, two printing apparatuses are selected for printing, the reference electrode 4 is spray-printed on the first apparatus, and the working electrode 2 and the counter electrode 3 are spray-printed on the second apparatus.

In conclusion, in actual production, a printing sequence of the working electrode 2, the counter electrode 3, and the reference electrode 4 may be correspondingly adjusted, which is not limited herein.

In S35, the outer surfaces of the substrate 1, the microneedles 6, the working electrode 2, the counter electrode 3, the reference electrode 4, and the enzyme are spray-printed by using biocompatible liquid and dried to form a biocompatible film.

Figure 6:
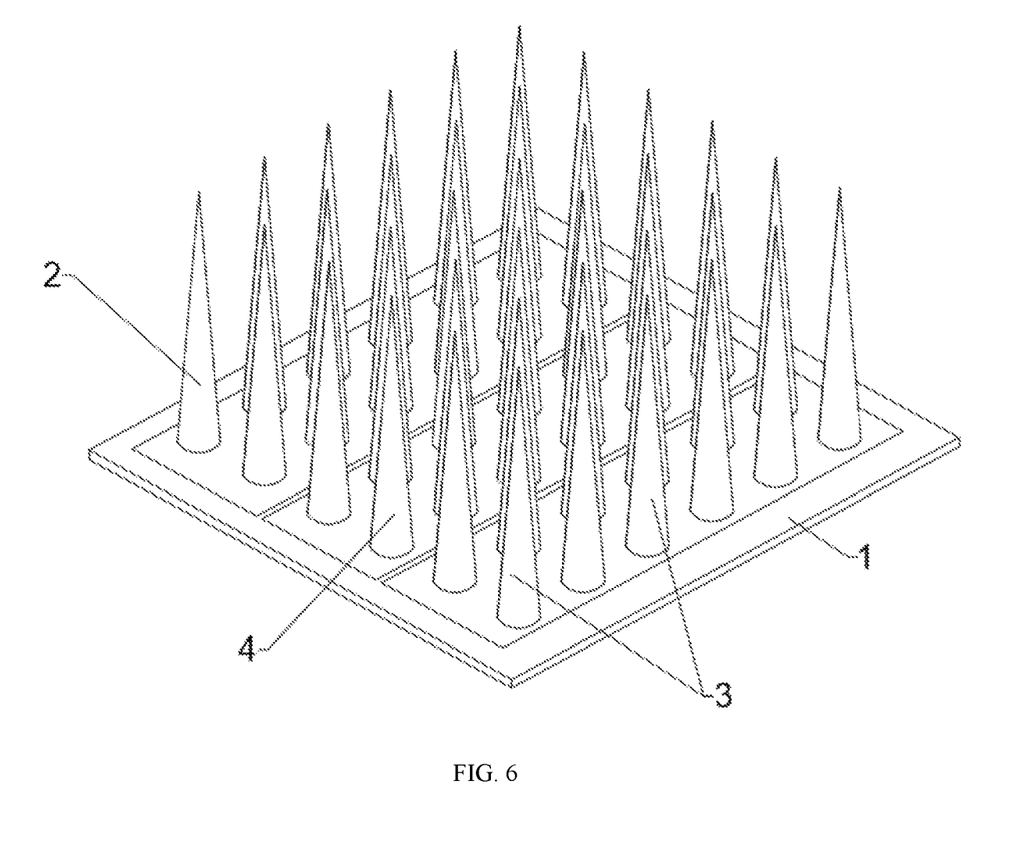
FIG. 6 is a structural schematic diagram of a partial perspective view of the first microneedle biosensor according to the present disclosure.
Figure 11:
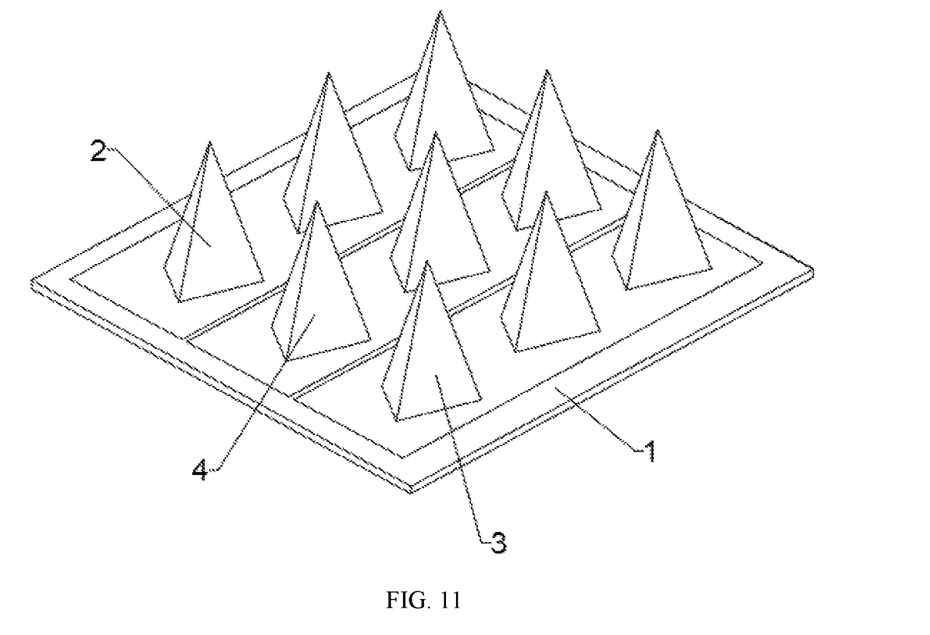
FIG. 11 is a structural schematic diagram of a partial perspective view of the fifth microneedle biosensor according to the present disclosure.

As shown in FIGS. 6 and 11, in an embodiment, at least three microneedles 6 are provided, and a working electrode 2, a counter electrode 3 and a reference electrode 4 correspond one-to-one to the microneedles 6.

The working electrode 2, the counter electrode 3 and the reference electrode 4 correspond one-to-one to the microneedles 6, for example, the working electrode 2 is arranged on the first microneedle, the counter electrode 3 is arranged on the second microneedle, and the reference electrode 4 is arranged on the third microneedle. The reference electrodes 4, the working electrodes 2 and the counter electrodes 3 are equal in number and are sequentially arranged side by side. As shown in FIG. 6, the reference electrodes 4, the working electrodes 2 and the counter electrodes 3 are each arranged in two rows, and each row is provided with six electrodes. Certainly, the number of rows of reference electrodes 4, working electrodes 2 and counter electrodes 3 and the number of electrodes in each row may be set according to use requirements.

As shown in FIG. 6, the microneedles 6 have a conical structure. As shown in FIG. 11, the microneedles 6 have a pyramidal structure.

Figure 8:
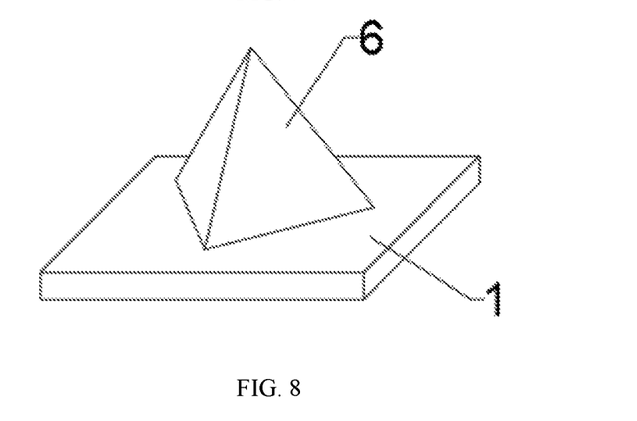
FIG. 8 is a structural schematic diagram of a partial perspective view of the third microneedle biosensor according to the present disclosure.
Figure 9:
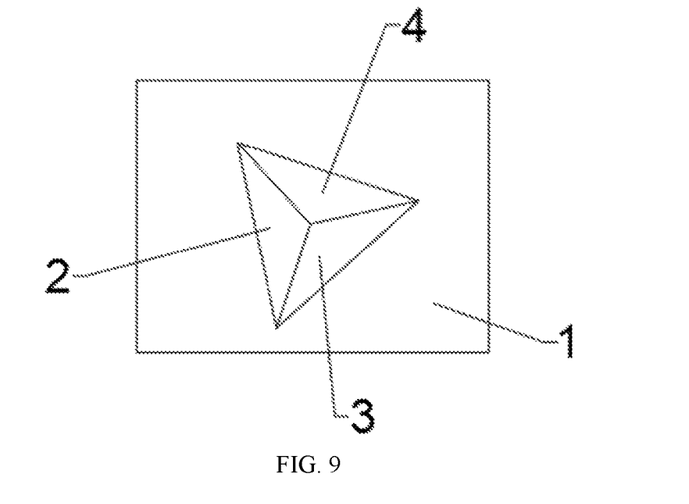
FIG. 9 is a structural schematic diagram of a partial top view of the microneedle biosensor as shown in FIG. 8.

As shown in FIGS. 8 and 9, in an embodiment, one microneedle 6 is provided and has a pyramidal structure, and a working electrode 2, a counter electrode 3 and a reference electrode 4 correspond one-to-one to surfaces of the microneedle 6.

When the microneedle 6 has a pyramidal structure, the microneedle has at least four surfaces, one surface is connected to the substrate 1, and the remaining at least three surfaces allow the corresponding working electrode 2, counter electrode 3 and reference electrode 4 to be printed separately. When one microneedle 6 is provided, a wound surface may be reduced, pain of a patient is reduced, and a production cost of the microneedle biosensor is reduced.

In an embodiment, the working electrode 2 is spray-printed by using a first ink, the counter electrode 3 is spray-printed by using a second ink, and the first ink and the second ink are both made of a nanogold composite material, or a nanoplatinum composite material, or a nanocarbon composite material.

The working electrode 2 is spray-printed by using a first ink, the counter electrode 3 is spray-printed by using a second ink, and the first ink and the second ink are both made of a nanogold composite material, or a nanoplatinum composite material, or a nanocarbon composite material, such that the working electrode 2 and the counter electrode 3 have desirable electrical conductivity.

In an embodiment, the reference electrode 4 is spray-printed by using a third ink, and the third ink is a nanoscale silver/silver chloride composite ink.

The third ink is a nanoscale silver/silver chloride composite ink, such that the reference electrode 4 has desirable electrical conductivity.

Figure 4:
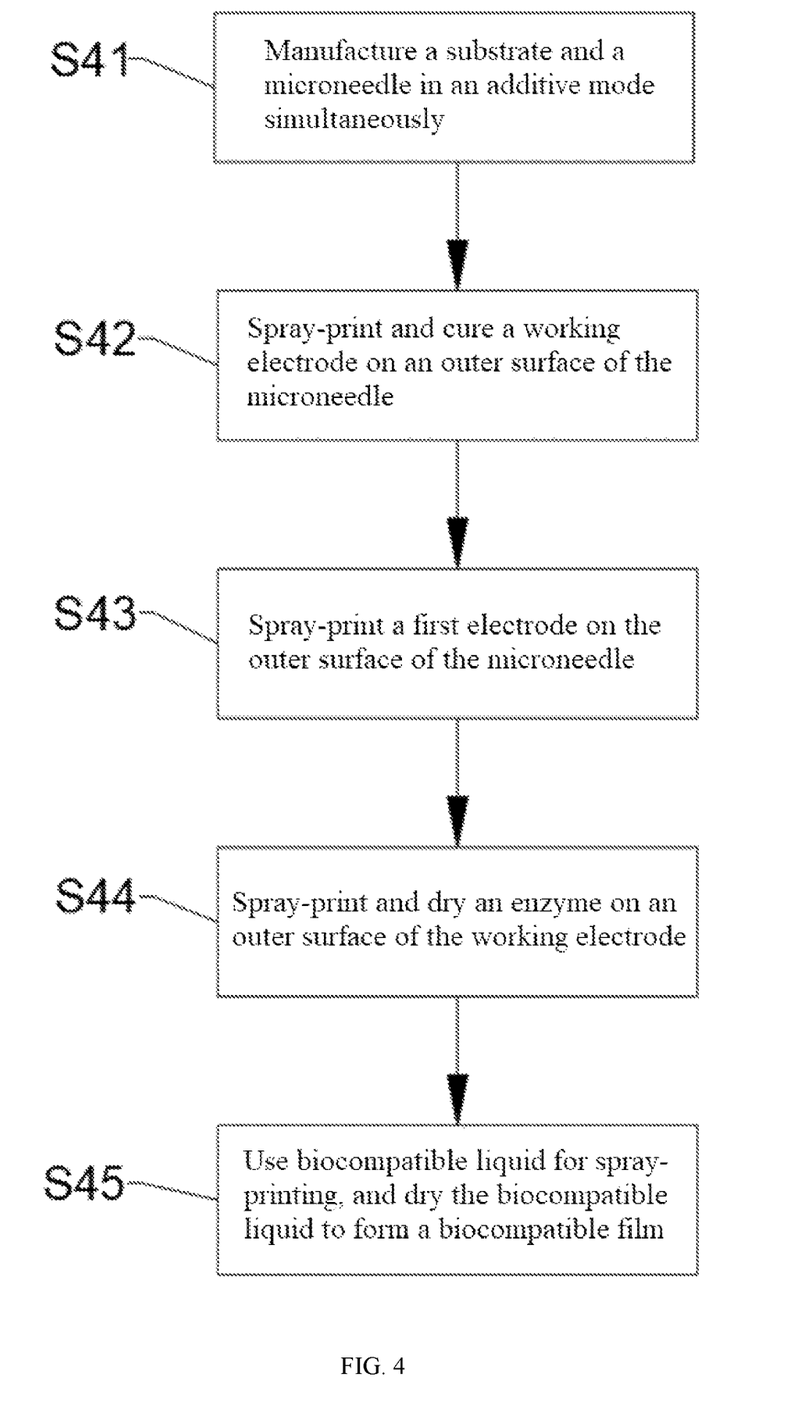
FIG. 4 is a flowchart of the fourth method for manufacturing a microneedle biosensor according to the present disclosure.

As shown in FIG. 4, in an embodiment, the method for manufacturing a microneedle biosensor includes:
- S41, manufacture a substrate 1 and a microneedle 6 in an additive mode simultaneously;
- S42, spray-print and cure a working electrode 2 on an outer surface of the microneedle 6;
- S43, spray-print and cure a first electrode 5 on the outer surface of the microneedle 6, where the first electrode 5 is used as both a reference electrode 4 and a counter electrode 3;
- S44, spray-print and dry an enzyme on an outer surface of the working electrode 2; and
- S45, use biocompatible liquid for spray-printing, and dry the biocompatible liquid to form the biocompatible film.

In actual production, two printing apparatuses are selected for printing, the working electrode 2 is spray-printed on the first apparatus, and the first electrode 5 is spray-printed on the second apparatus. Since the first electrode 5 is used as both the reference electrode 4 and the counter electrode 3, the working electrode 2 and the first electrode 5 are components in an electrochemical system and may be used in disease detection.

In S45, the outer surfaces of the substrate 1, the microneedles 6, the working electrode 2, the first electrode 5, and the enzyme are spray-printed by using biocompatible liquid and dried to form a biocompatible film.

Figure 5:
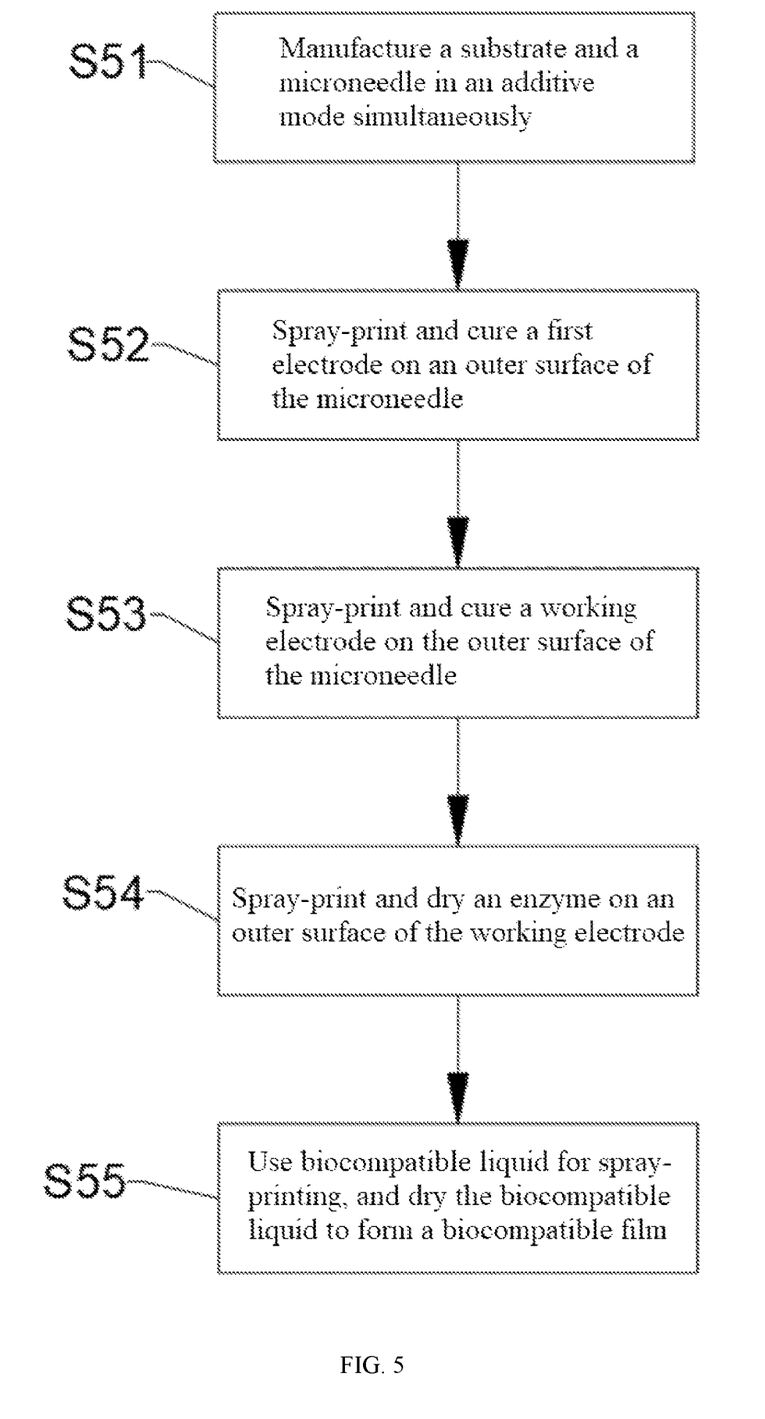
FIG. 5 is a flowchart of the fifth method for manufacturing a microneedle biosensor according to the present disclosure.

As shown in FIG. 5, in another embodiment, the method for manufacturing a microneedle biosensor includes:
- S51, manufacture a substrate 1 and a microneedle 6 in an additive mode simultaneously;
- S52, spray-print and cure a first electrode 5 on an outer surface of the microneedle 6, where the first electrode 5 is used as both a reference electrode 4 and a counter electrode 3;
- S53, spray-print and cure a working electrode 2 on an outer surface of the microneedle 6;
- S54, spray-print and dry an enzyme on an outer surface of the working electrode 2; and
- S55, use biocompatible liquid for spray-printing, and dry the biocompatible liquid to form the biocompatible film.

In S55, the outer surfaces of the substrate 1, the microneedles 6, the working electrode 2, the first electrode 5, and the enzyme are spray-printed by using biocompatible liquid and dried to form a biocompatible film.

Figure 7:
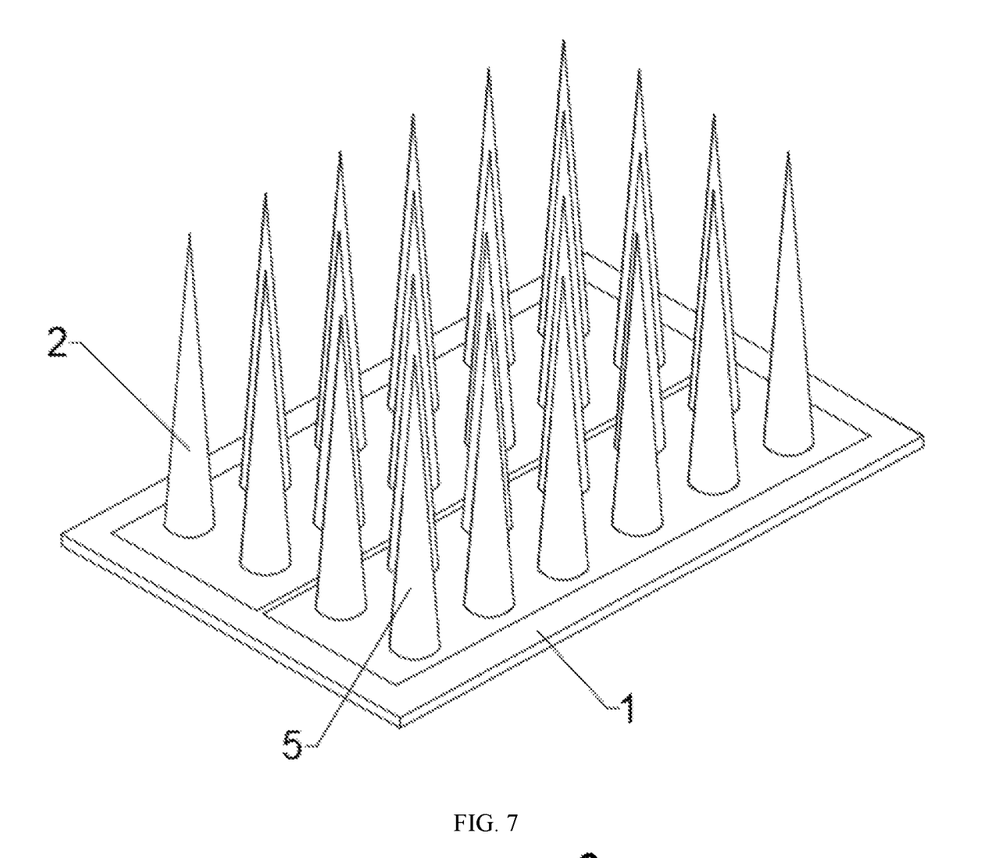
FIG. 7 is a structural schematic diagram of a partial perspective view of the second microneedle biosensor according to the present disclosure.
Figure 12:
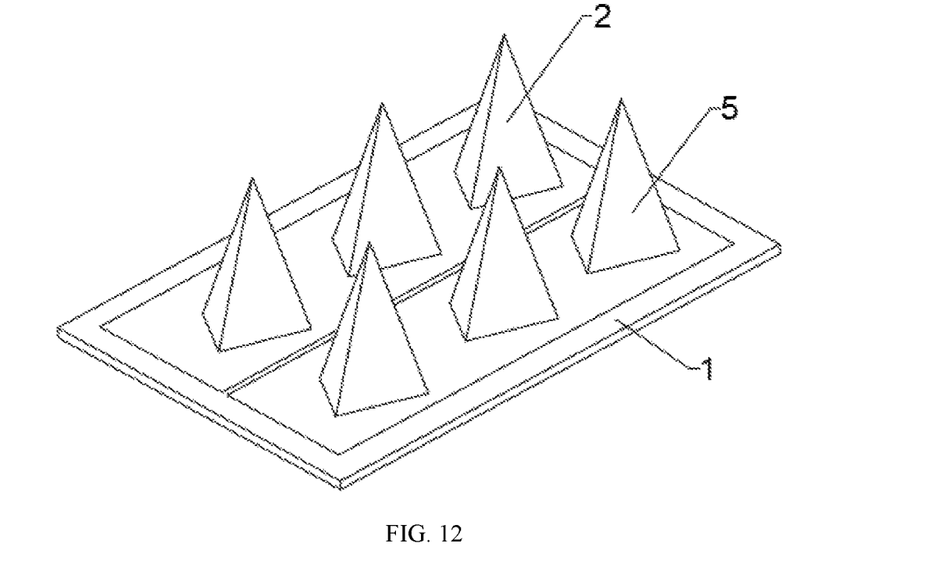
FIG. 12 is a structural schematic diagram of a partial perspective view of the sixth microneedle biosensor according to the present disclosure.

As shown in FIGS. 7 and 12, in an embodiment, at least two microneedles 6 are provided, and a working electrode 2 and a first electrode 5 correspond one-to-one to the microneedles 6.

The working electrode 2 and the first electrode 5 correspond one-to-one to the microneedles 6, for example, the working electrode 2 is arranged on the first microneedle, and the first electrode 5 is arranged on the second microneedle 6. The working electrodes 2 and the first electrodes 5 are equal in number and are sequentially arranged side by side. As shown in FIG. 7, the working electrodes 2 and the first electrodes 5 are each arranged in two rows, and each row is provided with six electrodes. The number of rows of working electrodes 2 and first electrodes 5 and the number of electrodes in each row may be set according to use requirements.

As shown in FIG. 7, the microneedles 6 have a conical structure. As shown in FIG. 12, the microneedles 6 have a pyramidal structure.

Figure 10:
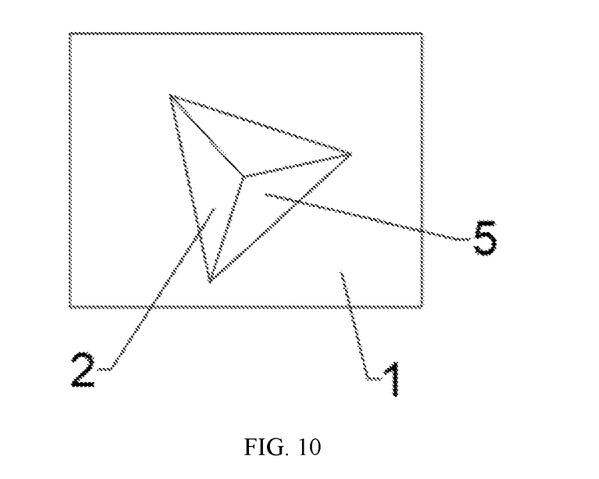
FIG. 10 is a structural schematic diagram of a partial top view of the fourth microneedle biosensor according to the present disclosure.

As shown in FIG. 10, in an embodiment, one microneedle 6 is provided and has a pyramidal structure, and a working electrode 2 and a first electrode 5 correspond one-to-one to surfaces of the microneedle 6.

When the microneedle 6 has a pyramidal structure, the microneedle has at least four surfaces, one surface is connected to the substrate 1, and two of the remaining at least three surfaces allow the corresponding working electrode and first electrode 5 to be printed separately. When one microneedle 6 is provided, a wound surface may be reduced, pain of a patient is reduced, and a production cost of the microneedle biosensor is reduced.

As shown in FIGS. 8-10, the microneedle 6 has a triangular pyramid structure. Certainly, the microneedle 6 may also have a rectangular pyramid structure, etc., which is not limited herein.

As shown in FIGS. 6 and 7, the microneedle 6 has a conical structure to facilitate insertion into a human body.

It will be appreciated that in practical applications, the microneedle 6 may also have other structures, for example, a pyramidal structure as shown in FIGS. 11 and 12, suitable for insertion into the human body. The arrangement and number of the microneedle 6 are arranged according to use requirements, which is not limited herein.

As shown in FIG. 1, in an embodiment, a working electrode 2 is spray-printed by using a first ink, and a first electrode 5 is spray-printed by using a third ink.

The working electrode 2 is spray-printed by using the first ink, and the first electrode 5 is spray-printed by using the third ink, such that the working electrode 2 and the first electrode 5 have desirable electrical conductivity.

As shown in FIG. 1, in an embodiment, the step of manufacturing the substrate 1 and the microneedle 6 in an additive mode simultaneously uses a biocompatible material.

Moreover, during additive manufacturing of the substrate 1 and the microneedle 6, damage to the human body when the microneedle 6 is broken in the body or is used does not need to be concerned due to use of a biocompatible material.

As shown in FIG. 1, in an embodiment, a first ink contains an electron mediator.

The electron mediator is a molecular conductor which transfers electrons generated in an enzyme reaction process from an enzyme reaction center to a surface of a working electrode 2 to make the working electrode 2 generate a corresponding current change. In this embodiment of the present application, the electron mediator is arranged in the working electrode 2.

In an embodiment, the electron mediator is Prussian blue.

Prussian blue, that is, ferric ferrocyanide, is a coordination compound with a chemical formula of $Fe_4[Fe(CN)_6]_3$ and has features of being stable at normal temperature and normal pressure, insoluble in water and soluble in acid and alkali. A working electrode 2 uses the Prussian blue, such that the working electrode 2 is also stable at normal temperature and normal pressure.

In another embodiment, the electron mediator may also be ferricyanide, quinhydrone, etc.

As shown in FIG. 1, in an embodiment, the step of spray-printing enzyme on an outer surface of the working electrode 2 uses a printing enzyme complex solution.

The enzyme participates in measurement. For different use environments, the enzyme types are different. For example, when the enzyme is used for diabetic patients, the enzyme is glucose oxidase, tissue fluid in the body contains glucose, in a working process, the glucose oxidase catalyzes a reaction between the glucose and oxygen to generate hydrogen peroxide, the hydrogen peroxide is subjected to an electrochemical reaction on the electrode, then the change of an electric signal is obtained, and concentration data of the glucose in the tissue fluid is obtained according to the change of the electric signal.

It will be appreciated that in practical applications, the microneedle 6 may be solid or hollow in order to achieve different functions. When the microneedle 6 is hollow, the microneedle 6 may also achieve an injection function, etc.

Apparently, the above embodiments are merely examples made for clarity of illustration and are not limiting of the implementation modes. It will be apparent to those of ordinary skill in the art that other changes or variations in different forms may be made in light of the above description. All implementation modes are not necessarily intended to be exhaustive. Apparent changes or variations derived therefrom are still within the scope of protection created by the present disclosure.

What is claimed is:

1. A method for manufacturing a microneedle biosensor, wherein the microneedle biosensor comprises a microneedle and a substrate, wherein one end of the microneedle is connected to the substrate, an outer surface of the microneedle is provided with a working electrode and a first electrode, an outer surface of the working electrode is provided with an enzyme, and an outer surface of the microneedle biosensor is covered with a biocompatible film; and the method for manufacturing the microneedle biosensor comprises:
   manufacturing the substrate and the microneedle in an additive manufacturing simultaneously;
   aerosol jet printing the working electrode and the first electrode on the outer surface of the microneedle, followed by drying;
   aerosol jet printing the enzyme on the outer surface of the working electrode; and using biocompatible liquid for jet-printing, and drying the biocompatible liquid to form the biocompatible film.

2. The method for manufacturing the microneedle biosensor according to claim 1, wherein the first electrode comprises a counter electrode and a reference electrode; and
   the step of printing the working electrode and the first electrode on the outer surface of the microneedle further comprises:
   aerosol jet printing the working electrode and the counter electrode on the outer surface of the microneedle simultaneously, and aerosol jet printing the reference electrode on the outer surface of the microneedle; and alternatively,
   aerosol jet printing the reference electrode on the outer surface of the microneedle, and
   aerosol jet printing the working electrode and the counter electrode on the outer surface of the microneedle simultaneously.

3. The method for manufacturing the microneedle biosensor according to claim 2, wherein the microneedle comprises a pyramidal structure and is provided with three surfaces, and wherein the working electrode corresponds to a first surface of the three surfaces of the pyramid structure, the counter electrode corresponds to a second surface of the three surfaces of the pyramid structure, and the reference electrode corresponds to a third surface of the three surfaces of the microneedle.

4. The method for manufacturing the microneedle biosensor according to claim 2, wherein:
   the working electrode is jet-printed by using a first ink,
   the counter electrode is jet-printed by using a second ink, and
   the first ink and the second ink are selected from a group consisting of a nanogold composite material, or a nanoplatinum composite material, or a nanocarbon composite material.

5. The method for manufacturing the microneedle biosensor according to claim 4, wherein the reference electrode is jet-printed by using a third ink, and the third ink is a nanoscale silver/silver chloride composite ink.

6. The method for manufacturing the microneedle biosensor according to claim 1, wherein the step of jet-printing the working electrode and the first electrode on the outer surface of the microneedle comprises:
   aerosol jet printing the working electrode on the outer surface of the microneedle, and
   aerosol jet printing the first electrode on the outer surface of the microneedle, wherein the first electrode is used as both a reference electrode and a counter electrode; and alternatively,
   aerosol jet printing the first electrode on the outer surface of the microneedle, and aerosol jet printing the working electrode on the outer surface of the microneedle.

7. The method for manufacturing the microneedle biosensor according to claim 6, wherein the microneedle comprises a pyramidal structure and is provided with three surfaces, and wherein the working electrode corresponds to a first surface of the three surfaces of the pyramid structure, and the first electrode having the reference electrode and the counter electrode correspond second and third surfaces of the microneedle.

8. The method for manufacturing the microneedle biosensor according to claim 6, wherein the working electrode is jet-printed by using a first ink, and the first electrode is jet-printed by using a third ink.

9. The method for manufacturing the microneedle biosensor according to claim 4, wherein the first ink contains an electron mediator.

10. The method for manufacturing the microneedle biosensor according to claim 2, wherein:
    the working electrode is jet-printed by using a first ink,
    the counter electrode is jet-printed by using a second ink, and
    the first ink and the second ink are both-selected from a group consisting of a nanogold composite material, or a nanoplatinum composite material, or a nanocarbon composite material.

11. The method for manufacturing the microneedle biosensor according to claim 3, wherein:
    the working electrode is jet-printed by using a first ink,
    the counter electrode is jet-printed by using a second ink, and the first ink and the second ink are selected from a group consisting of a nanogold composite material, or a nanoplatinum composite material, or a nanocarbon composite material.

12. The method for manufacturing the microneedle biosensor according to claim 1, wherein the microneedle comprises a conical structure.

13. The method for manufacturing the microneedle biosensor according to claim 1, wherein the microneedle comprises a pyramid structure.

* * * * *